US00PP33146P2

(12) United States Plant Patent
Van Swieten

(10) Patent No.: US PP33,146 P2
(45) Date of Patent: Jun. 8, 2021

(54) ***PHALAENOPSIS* ORCHID PLANT NAMED 'PHALGRUSEI'**

(50) Latin Name: ***Phalaenopsis* hybrid**
Varietal Denomination: PHALGRUSEI

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/930,934

(22) Filed: Jul. 16, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database 20210113, retrieved on Jan. 13, 2021, retrieved from the Internet at https://www.upov.int/pluto/en/index.jsp, one page. (Year: 2021).*

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALGRUSEI', particularly characterized by white, striped flowers with white, striped and extra-large lips, inflorescence length of 340.0 mm to 430.0 mm, flower longevity on the plant of about 22 weeks, and is propagated by meristem tissue culture, is disclosed.

3 Drawing Sheets

Genus and species: *Phalaenopsis* hybrid.
Variety denomination: 'PHALGRUSEI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGRUSEI'.

The new *Phalaenopsis* plant is a product of a planned breeding program conducted by the inventor in Bleiswijk, the Netherlands. The objective of this breeding program was to create a new *Phalaenopsis* plant with white, striped flowers having white, striped and extra-large lips, suitable for potted plant production.

The new *Phalaenopsis* plant 'PHALGRUSEI' is a result of cross-pollination made by the inventor in April 2010 in Bleiswijk, the Netherlands, of the proprietary female, or seed parent, *Phalaenopsis* hybrid '6541-01' (unpatented) with the proprietary male, or pollen parent, *Phalaenopsis* hybrid '01-3402' (unpatented).

The new *Phalaenopsis* was selected by the inventor as a single plant within the progeny of the stated cross-pollination in a controlled greenhouse in Bleiswijk, the Netherlands, in January 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 25, 2018 (Application no. 2018/2462), by Applicant who obtained the subject matter disclosed directly from the inventor. 'PHALGRUSEI' has not been made publicly available or sold anywhere in the world prior to the effective filing date of this application with the exception of sales or disclosures made one year or less before the effective filing date of this claimed invention by Applicant who obtained 'PHALGRUSEI' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGRUSEI' as a new and distinct variety of *Phalaenopsis* plant:

1) White, striped flowers with white, striped and extra-large lips;
2) Inflorescence length is 340.0 mm to 430.0 mm; and
3) Flower longevity on the plant is about 22 weeks.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2020. Colors in the photographs may differ from the color values cited in the detailed botanical description, which accurately describe the actual colors of the new variety.

DESCRIPTION OF THE NEW VARIETY

Figure 1:
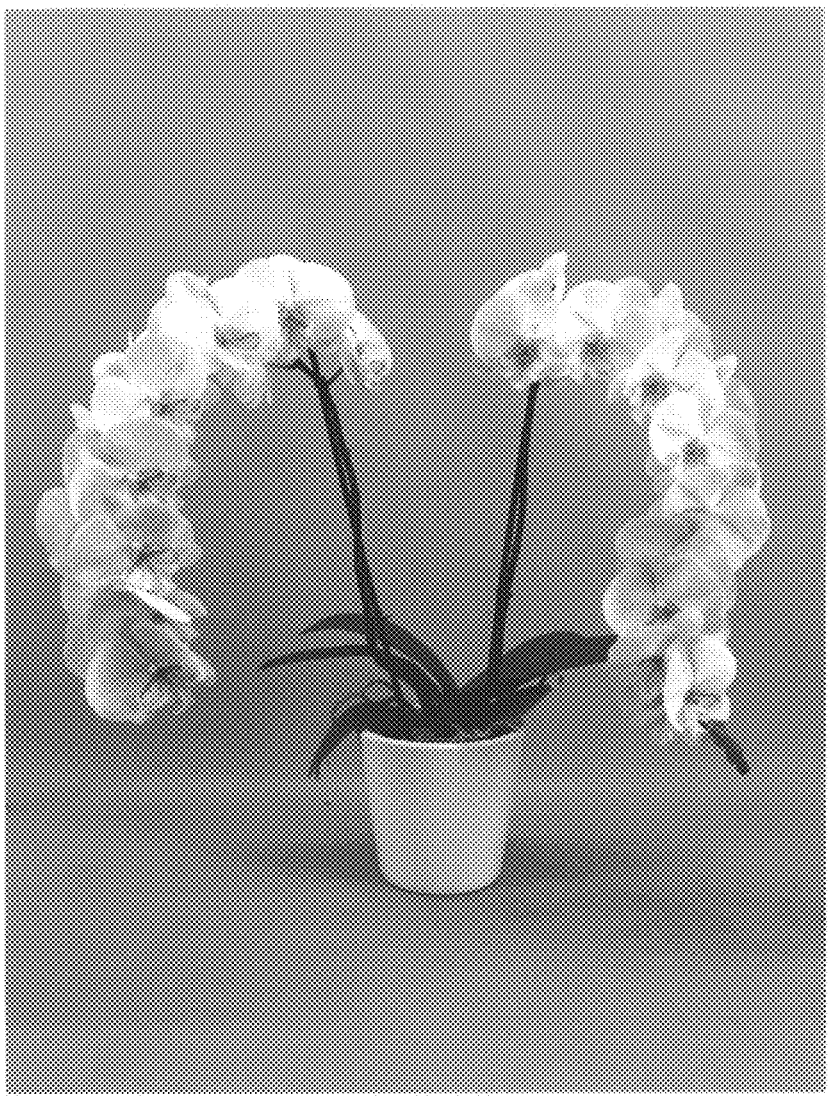
FIG. 1 shows the overall plant habit, including blooms, buds, and foliage of 'PHALGRUSEI'.
Figure 2:
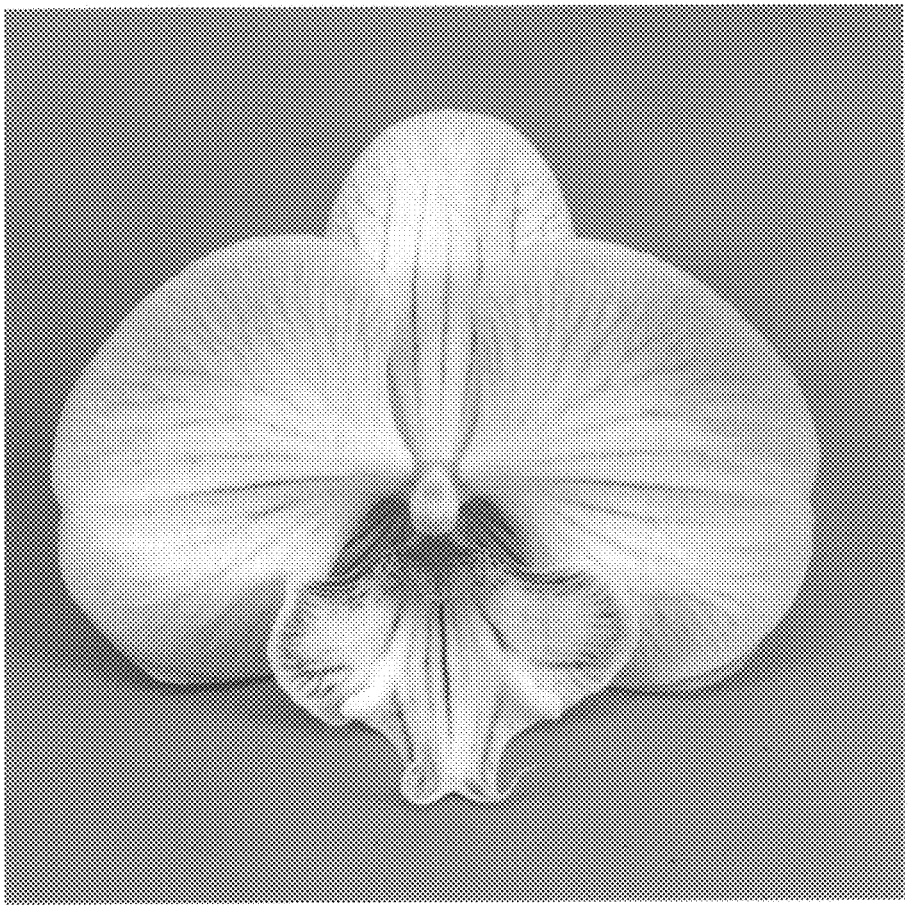
FIG. 2 shows a close-up of a flower of 'PHALGRUSEI'.
Figure 3:
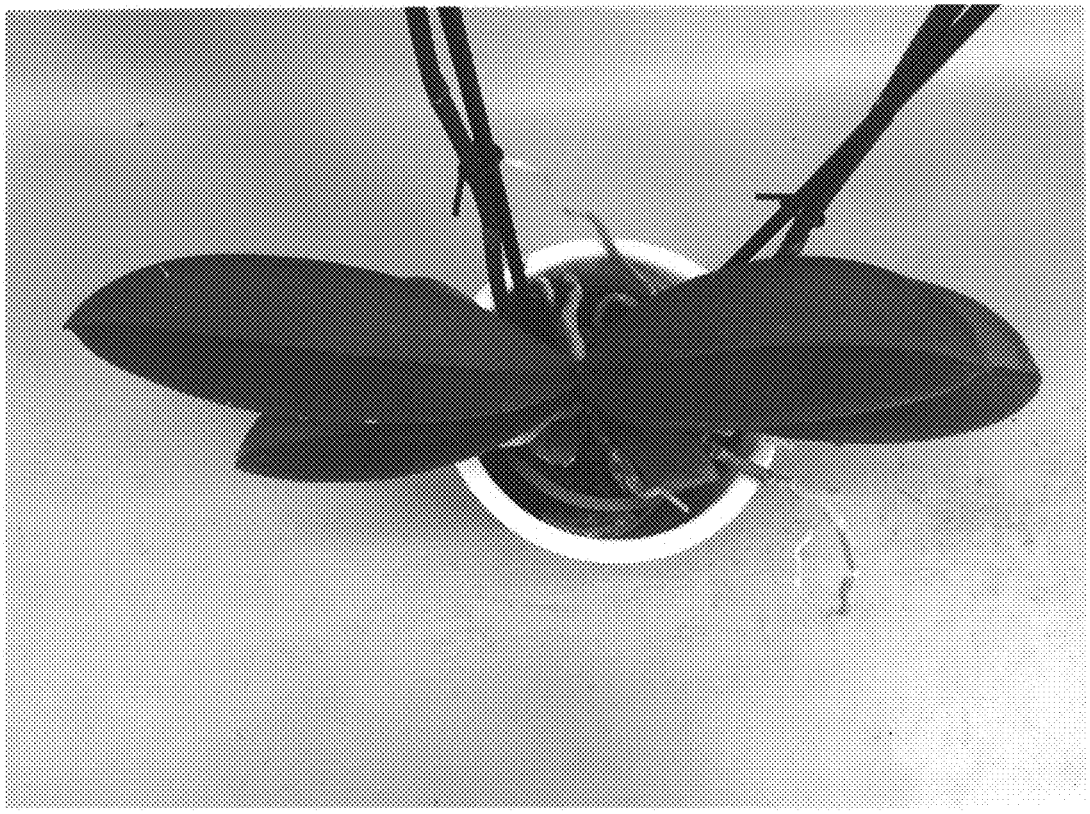
FIG. 3 shows an overhead view of the leaves of 'PHALGRUSEI'.

The following detailed description sets forth the distinctive characteristics of 'PHALGRUSEI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALGRUSEI'.

Parentage:

*Female parent.*—*Phalaenopsis* cultivar '6541-01' (unpatented).

*Male parent.*—*Phalaenopsis* cultivar '01-3402' (unpatented).

Propagation:

*Type.*—Meristem tissue culture.

Roots:

*Root description.*—Greyed-green (something between RHS 190B and 190C) colored roots with branching lateral roots having light yellow-green (RHS 145C) with a hint of purplish-red (RHS N77B) colored root tips.

Plant:

*Commercial crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme inflorescence.

*Height (from soil level to top of inflorescence).*—Approximately 65.0 cm to 70.0 cm.

*Width (measured from leaf tips).*—About 37.0 cm to 39.0 cm.

*Vigor.*—Strong.

Leaves:

*Mature leaves.*—Quantity per plant: 7 to 8 leaves are produced before flowering. Length (fully expanded): 18.0 cm to 20.0 cm. Width: 6.0 cm to 7.0 cm. Position of the broadest part of the leaf: At the middle. Shape: Oblong. Base shape: Moderately elongated. Apex: Unequal acute. Leaf blade angle with the petiole (measured from the horizontal position): Between 20 degrees and 35 degrees. Leaf margin: Entire. Color: Upper surface: RHS 146A. Lower surface: RHS 146B and reddish-brown (RHS 200B) toward the margin. Texture (both upper and lower surfaces): Smooth. Thickness: 2.3 mm to 2.7 mm. Variegation: Absent. Venation: Pattern: Parallel. Color of the midvein: Upper surface: RHS 146A. Lower surface: RHS 146B.

Peduncle:

*Quantity per plant.*—1 to 2.

*Number of flowers per peduncle.*—13 to 19.

*Length.*—65.0 cm to 70.0 cm.

*Diameter.*—5.5 mm to 6.0 mm.

*Strength.*—Strong.

*Aspect.*—Upright to slightly pendent.

*Texture.*—Smooth.

*Color.*—Mix of reddish-brown (RHS 200A) and yellow-green (RHS 146B).

*Internode length.*—2.5 cm to 3.5 cm.

Inflorescence description:

*Appearance.*—Upright to slightly pendent, raceme inflorescence with bilaterally symmetrical flowers that open in succession beginning with the lowermost flower.

*Number of inflorescences.*—1 to 2.

*Inflorescence size.*—Height (from base to tip): 340.0 mm to 430.0 mm.

*Flowering time.*—First flowers can be expected 10 to 11 months after planting in a 12-cm pot.

*Flower.*—Height: 78.0 mm to 83.0 mm. Diameter: 90.0 mm to 95.0 mm. Depth of lip: about 15.0 mm to 20.0 mm.

*Flower longevity.*—On the plant: 21 to 23 weeks.

*Flower shape.*—Concave.

*Fragrance.*—Absent.

*Flower bud.*—Average size: Large. Length: 26.0 mm to 28.0 mm. Width: 20.0 mm to 22.0 mm. Shape: Egg shaped. Color: Light yellow-green (RHS 145C) with a hint of purplish-red (RHS N77B).

*Petals.*—Arrangement: Open/free. Shape: Semi-circular. Apex: Emarginated asymmetric. Margin: Weakly undulated. Length (from base to tip): 44.0 mm to 46.0 mm. Width: 57.0 mm to 59.0 mm. Position of the broadest part of the petal: Toward the base. Color (when fully opened): Upper surface: Basic color: White (RHS NN155C). Over color: Purplish-red stripes (RHS N78C). Lower surface: Basic color: White (RHS NN155C). Over color: Diluting light purple stripes (something in between RHS 76A and 76B). Number of spots and stripes on the petals (upper surface): Many stripes. Color of spots and stripes on the petals (upper surface): RHS N78C. Density of netting of the petals (upper surface): None. Color of the netting (upper surface): Not applicable.

*Dorsal sepal.*—Shape: Elliptic. Apex: Slightly obtuse to rounded symmetric. Margin: Entire. Length (from base to tip): 46.0 mm to 48.0 mm. Width: 34.0 mm to 36.0 mm. Position of the broadest part of the dorsal sepals: At the middle. Color (when fully opened): Upper surface: Basic color: White (RHS NN155C). Over color: Purplish-red stripes (RHS N78C). Lower surface: Basic color: White (RHS NN155C). Over color: Diluting light purple stripes (something in between RHS 76A and 76B). Number of spots and stripes on the dorsal sepals (upper surface): Many stripes. Color of spots and stripes on the dorsal sepals (upper surface): RHS N78C. Density of netting of the dorsal sepals (upper surface): None. Color of the netting: Not applicable.

*Lateral sepals.*—Shape: Ovate. Apex: Obtuse symmetric. Margin: Entire. Length (from base to tip): 45.0 mm to 47.0 mm. Width: 27.0 mm to 29.0 mm. Position of the broadest part of the lateral sepals: At the base. Color (when fully opened): Upper surface: Basic color: White (RHS NN155C). Over color: Hint of light yellow-green (RHS 145C) at the base; striped (RHS N78B and N78C). Lower surface: Basic color: White (RHS NN155C). Over color: Light yellow-green (RHS 145D) at the base and diluting light purple stripes (something in between RHS 76A and 76B). Number of spots and stripes on the lateral sepals (upper surface): Many stripes. Color of spots and stripes on the lateral sepals (upper surface): RHS N78B and N78C. Density of netting of the lateral sepals (upper surface): None. Color of the netting (upper surface): Not applicable.

*Labellum* (*lip*).—Overall shape: Three-lobed with callus at central junction of the lateral lobes and base of the apical lobe. The apical lobe is terminated by two whiskers. Lateral lobes and apical lobe are connected. Whiskers: Present. Length of whiskers: 11.0 mm to 13.0 mm. Color of whiskers: White (RHS NN155C). Pubescence on the lip: Absent.

*Lateral lobe.*—Margin: Undulated. Length: 21.0 mm to 23.0 mm. Width: 18.0 mm to 20.0 mm. Color: Upper surface: Hint of yellow-green (RHS 154A) and purplish-red dots (RHS 186B) at the base toward the callus (RHS 154A); white (RHS NN155C) toward the margin with reddish-purple stripes (something in between RHS N78B and N78C). Lower surface: White (RHS NN155C) with a hint of light purple (RHS 76B) toward the margin. Number of spots, dots, and stripes on the lateral lobe: Few small dots at the base and medium to many stripes toward margin. Color of spots, dots, and stripes on the lateral lobe: Dots (RHS 186B) and stripes (something in between RHS N78B and N78C). Density of netting of the lateral lobe: None. Color of the netting: Not applicable.

*Apical lobe.*—Shape: Trapezoid. Margin: Entire. Length: 23.0 mm to 25.0 mm. Width: 30.0 mm to 32.0 mm. Color: Upper surface: White (RHS NN155C) with reddish-purple midvein (RHS N78A) and purplish-pink stripes (RHS N78C). Lower surface: White (RHS NN155C) with very light purple shade (RHS 76B) and light purple midvein (RHS 76A). Number of spots and stripes on the apical lobe: Medium stripes. Color of spots and stripes on the apical lobe: RHS N78C. Density of netting of the apical lobe: None. Color of the netting: Not applicable.

*Callus.*—Average size: Small. Height: 4.0 mm to 5.0 mm. Length: 4.0 mm to 5.0 mm. Width: 3.0 mm to 4.0 mm. Color: Yellow-green (RHS 154A); dotted (RHS 186B).

Reproductive organs:

*Column.*—Length: 8.0 mm to 10.0 mm. Diameter: 5.0 mm to 5.3 mm. Color: White (RHS NN155C) with small purplish-pink region (RHS N78C) at the middle.

*Pollinia.*—Quantity: 2. Diameter: 1.1 mm to 1.3 mm. Color: Orange (RHS N25B).

*Ovary.*—Length: 7.0 mm to 9.0 mm. Diameter: 2.1 mm to 2.3 mm.

*Pedicel.*—Length: 28.0 mm to 30.0 mm. Diameter: 2.4 mm to 2.6 mm. Texture: Smooth. Color: Light yellow-green (from RHS 145B to 145C) at the base; very light purple (something in between RHS 76C and 76D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGRUSEI' differs from female parent plant '6541-01' (unpatented) in that 'PHALGRUSEI' has a striped flower pattern and extra-large lips, whereas '6541-01' has an even flower pattern and typical lips.

'PHALGRUSEI' differs from male parent plant '01-3402' (unpatented) in that 'PHALGRUSEI' has a striped flower pattern, whereas '01-3402' has a striped and shaded flower pattern. Additionally, 'PHALGRUSEI' has larger flowers than '01-3402'.

'PHALGRUSEI' is most similar to the commercial *Phalaenopsis* plants named 'PHALGATYH' (U.S. Plant Pat. No. 30,885) and 'PHALGTAWI' (U.S. Plant Pat. No. 32,205). 'PHALGRUSEI' differs from the commercial variety 'PHALGATYH' in that 'PHALGRUSEI' has flowers with a main color of white and a striped pattern, whereas 'PHALGATYH' has flowers with a main color of very light purple and a striped and edged pattern. Additionally, 'PHALGRUSEI' has larger flowers than 'PHALGATYH'.

'PHALGRUSEI' differs from the commercial variety 'PHALGTAWI' in that 'PHALGRUSEI' has flowers with an open/free arrangement and a main color of white, whereas 'PHALGTAWI' has flowers with an overlapping arrangement and a main color of reddish-purple. Additionally, 'PHALGRUSEI' has smaller flowers than 'PHALGTAWI'.

I claim:

1. A new and distinct variety of *Phalaenopsis* plant named 'PHALGRUSEI', substantially as described and illustrated herein.

* * * * *